United States Patent
Popov et al.

(10) Patent No.: US 7,909,772 B2
(45) Date of Patent: Mar. 22, 2011

(54) NON-INVASIVE MEASUREMENT OF SECOND HEART SOUND COMPONENTS

(75) Inventors: Boris Popov, Montreal (CA); Victor F. Lanzo, Laval (CA); Rajeev Agarwal, Dollard-des-Ormeaux (CA)

(73) Assignee: Masimo Corporation, Irvine, CA (US)

( * ) Notice: Subject to any disclaimer, the term of this patent is extended or adjusted under 35 U.S.C. 154(b) by 860 days.

(21) Appl. No.: 11/578,462

(22) PCT Filed: Apr. 15, 2005

(86) PCT No.: PCT/CA2005/000568
§ 371 (c)(1),
(2), (4) Date: Aug. 13, 2007

(87) PCT Pub. No.: WO2005/099562
PCT Pub. Date: Oct. 27, 2005

(65) Prior Publication Data
US 2008/0091115 A1    Apr. 17, 2008

Related U.S. Application Data

(60) Provisional application No. 60/562,538, filed on Apr. 16, 2004.

(30) Foreign Application Priority Data

Apr. 16, 2004   (CA) ..................................... 2464634

(51) Int. Cl.
A61B 5/02    (2006.01)

(52) U.S. Cl. ................ 600/528; 600/485; 600/586
(58) Field of Classification Search ................. 600/528, 600/485
See application file for complete search history.

(56) References Cited

U.S. PATENT DOCUMENTS

| | | | |
|---|---|---|---|
| 6,050,950 A | 4/2000 | Mohler | |
| 6,179,783 B1 | 1/2001 | Mohler | |
| 6,245,025 B1 | 6/2001 | Torok et al. | |
| 6,368,283 B1 * | 4/2002 | Xu et al. | ...... 600/485 |

OTHER PUBLICATIONS

Adaptive Segmentation of Electroencephalographic Data using Non-Linear Energy Operator (Agarwal et al., Proceedings of IEEE '99, ISCAS'99, Orlando, Florida, 1999).

* cited by examiner

Primary Examiner — Carl H. Layno
Assistant Examiner — Jon-Eric C. Morales
(74) Attorney, Agent, or Firm — Law Office of Glenn R. Smith (57) ABSTRACT

A method and apparatus for estimating a location of pulmonary and aortic components of second heart sounds of a patient over an interval. The method comprises the steps of producing an electronic representation of heart sounds of the patient over the interval, identifying at least one second heart sound in the interval using the electronic representation, for each identified second heart sound generating an estimated value for a location of the aortic component and the pulmonary component. There is also included a method for using the estimated location of the aortic component and the pulmonary component for estimation of the blood pressure in the pulmonary artery of a patient.

5 Claims, 4 Drawing Sheets

NON-INVASIVE MEASUREMENT OF SECOND HEART SOUND COMPONENTS

RELATED APPLICATIONS

This application is the national stage of International Application No. PCT/CA2005/000568, filed Apr. 15, 2005, which claims the benefit of and priority from U.S. Provisional No. 60/562,538, filed Apr. 16, 2004, which are incorporated by reference herein.

FIELD OF THE INVENTION

The present invention relates to a method and apparatus for non-invasive detection of second heart sound (S2) components. In particular, the present invention relates to a method and apparatus for estimating a location of the aortic (A2) and pulmonary (P2) components of S2 relative to the Q marker of a QRS segment of an Electrocardiogram (ECG).

BACKGROUND OF THE INVENTION

The highly publicized problem of cardio-vascular diseases, an increased population living excess of 80, and the predominance of the heart disease as a leading cause of death have increased the importance of the clinical practioner's ability to recognize abnormal heart conditions. One of the most powerful instruments for non-invasive heart diagnostics is auscultation. Traditionally, auscultation is based on a physician's ability to use a stethoscope to recognize specific patterns and phenomena. Through advances in technology many of these abilities have been automated, however for some of these auscultation methods a stable automated procedure has yet to be found.

For diagnostic cardiac events one of the most interesting sounds is the second heart sound This sound comprises two components which are generally of interest: the aortic component and the pulmonary component. Detection and recognition of those components provides the possibility of measuring the systole and diastole duration for both the left- and right heart. These values are very important for many applications such as detection of pulmonary artery hypertension, dysfunction of heart valves, left and right ventricular dysfunction, etc.

As described hereinabove, the second heart sound and the components A2 and P2 thereof have significant clinical value. However, these components are very often masked by noises and other acoustic components of both the heart sounds and other parts of human body. As result, typically only specially trained and experienced clinicians can distinguish the A2 and P2 components. As a result, an automated computer-based procedure for A2 and P2 components would be desirable in clinical practice. One prior art reference, U.S. Pat. No. 6,368,283, reveals such a method. However, the proposed method is a non-automated human-assisted procedure which only works during periods of non-breathing.

Cardiac catheterisation and echocardiography, which have provided an accurate diagnosis of both right- and left heart abnormalities, have added a new dimension to usefulness of the phonocardiogram in assessing the presence and severity of cardiovascular abnormalities. Although cardiac catheterization generally provides the decisive evidence of the presence and severity of cardiac abnormalities, the external sound recordings correlate sufficiently well with the internal findings for them to serve, in many instances, as diagnostic tool per se. In this regard, phonocardiography often provides information complementary to that obtained by echocardiography. With this enhanced diagnostic accuracy, simpler and less painful external techniques can be used to determine when a patient needs more extensive cardiac treatment. Even in those cases where cardiac catheterisation is deemed necessary, the knowledge gained beforehand through phonocardiography and other non-invasive studies can lead to much more efficient and fruitful invasive study.

SUMMARY OF THE INVENTION

To address the above and other drawbacks, there is provided a method for estimating a location of pulmonary and aortic components of second heart sounds of a patient over an interval. The method comprises the steps of producing an electronic representation of heart sounds of the patient over the interval, identifying at least one second heart sound in the interval using the electronic representation, for each identified second heart sound calculating a frequency weighted energy (FWE), normalising the FWE, identifying peaks in the FWE, determining a maximum peak from the identified peaks and retaining the maximum peak and peaks having an amplitude within a predetermined amount of an amplitude of the maximum peak, wherein if two or more peaks are retained, two largest peaks are selected, a first peak as a candidate value for the aortic component and a second peak as a candidate value for the pulmonary component, wherein the first peak is prior to the second peak and wherein if only a single peak is retained, the single peak is selected as a candidate value for the aortic component, and generating an estimated value for a location of the aortic component and the pulmonary component from the candidate values.

There is also provided a method for estimating a location of pulmonary and aortic components of second heart sounds of a patient over an interval. The method comprises the steps of producing an electronic representation of heart sounds of the patient over the interval, dividing the electronic representation into a plurality of sub-channels, for each of the sub-channel representations, identifying at least one second heart sound in the interval using the electronic representation and extracting an estimated location of a sub-channel aortic component and a sub-channel pulmonary component from the at least one second heart sound, combining the estimated sub-channel aortic component locations to form the estimated aortic component location and the estimated sub-channel pulmonary component locations to form the estimated pulmonary component location.

Additionally, there is provided a method for estimating a location of pulmonary and aortic components of second heart sounds a patient over an interval. The method comprises the steps of positioning a first transducer at a first position on the patient, the first transducer producing a first electronic representation of heart sounds of the patient over the interval, positioning a second transducer at a second position on the patient, the second transducer producing a second electronic representation of heart sounds of the patient over the interval, for the first electronic representation identifying at least one second heart sound in the interval, for each identified second heart sound calculating a FWE, normalising the FWE, identifying peaks in the FWE, determining a maximum peak from the identified peaks and retaining the maximum peak and peaks having an amplitude within a predetermined amount of an amplitude of the maximum peak, wherein if two or more peaks are retained, two largest peaks are selected, a first peak as a candidate value for the aortic component and a second peak as a candidate value for the pulmonary component, wherein the first peak is prior to the second peak and wherein if only a single peak is retained, the single peak is selected as a candidate value for the aortic component, and generating a first estimated value for a location of an aortic component and a pulmonary component from the candidate values and for the second electronic representation identifying at least one second heart sound in the interval, for each identified second heart sound calculating a FWE, normalising the FWE, identifying peaks in the FWE, determining a maximum peak from the identified peaks and retaining the maximum peak and peaks having an amplitude within a predetermined amount of an amplitude of the maximum peak, wherein if two or more peaks are retained, two largest peaks are selected, a first peak as a candidate value for the aortic component and a second peak as a candidate value for the pulmonary component, wherein the first peak is prior to the second peak and wherein if only a single peak is retained, the single peak is selected as a candidate value for the aortic component and generating second estimated values for a location of the aortic component and the pulmonary component from the candidate values and combining the first and second estimated aortic location values and the first and second estimated pulmonary location values wherein the estimated location of the aortic components is the combined first and second estimated aortic location values and the estimated location of the pulmonary components is the combined first and second estimated pulmonary location values.

Furthermore, there is provided a method for estimating pulmonary artery pressure of a patient over an interval. The method comprises the steps of producing an electronic representation of heart sounds of the patient over the interval, identifying at least one second heart sound in the interval using the electronic representation, for each identified second heart sound calculating a FWE, normalising the FWE, identifying peaks in the FWE, determining a maximum peak from the identified peaks and retaining the maximum peak and peaks having an amplitude within a predetermined amount of an amplitude of the maximum peak, wherein if two or more peaks are retained, two largest peaks are selected, a first peak as a candidate value for the aortic component and a second peak as a candidate value for the pulmonary component, wherein the first peak is prior to the second peak and wherein if only a single peak is retained, the single peak is selected as a candidate value for the aortic component and generating an estimated value for a location of an aortic component and a location of pulmonary component from the candidate values, determining a splitting interval as a time between the aortic component location and the pulmonary component location, normalising the splitting interval, and estimating the systolic pulmonary artery pressure using a predetermined function which describes a relationship between the normalised splitting interval and the systolic and diastolic pulmonary artery pressures.

Also, there is provided an apparatus implementing any of the above methods.

DETAILED DESCRIPTION OF THE ILLUSTRATIVE EMBODIMENTS

Figure 1:
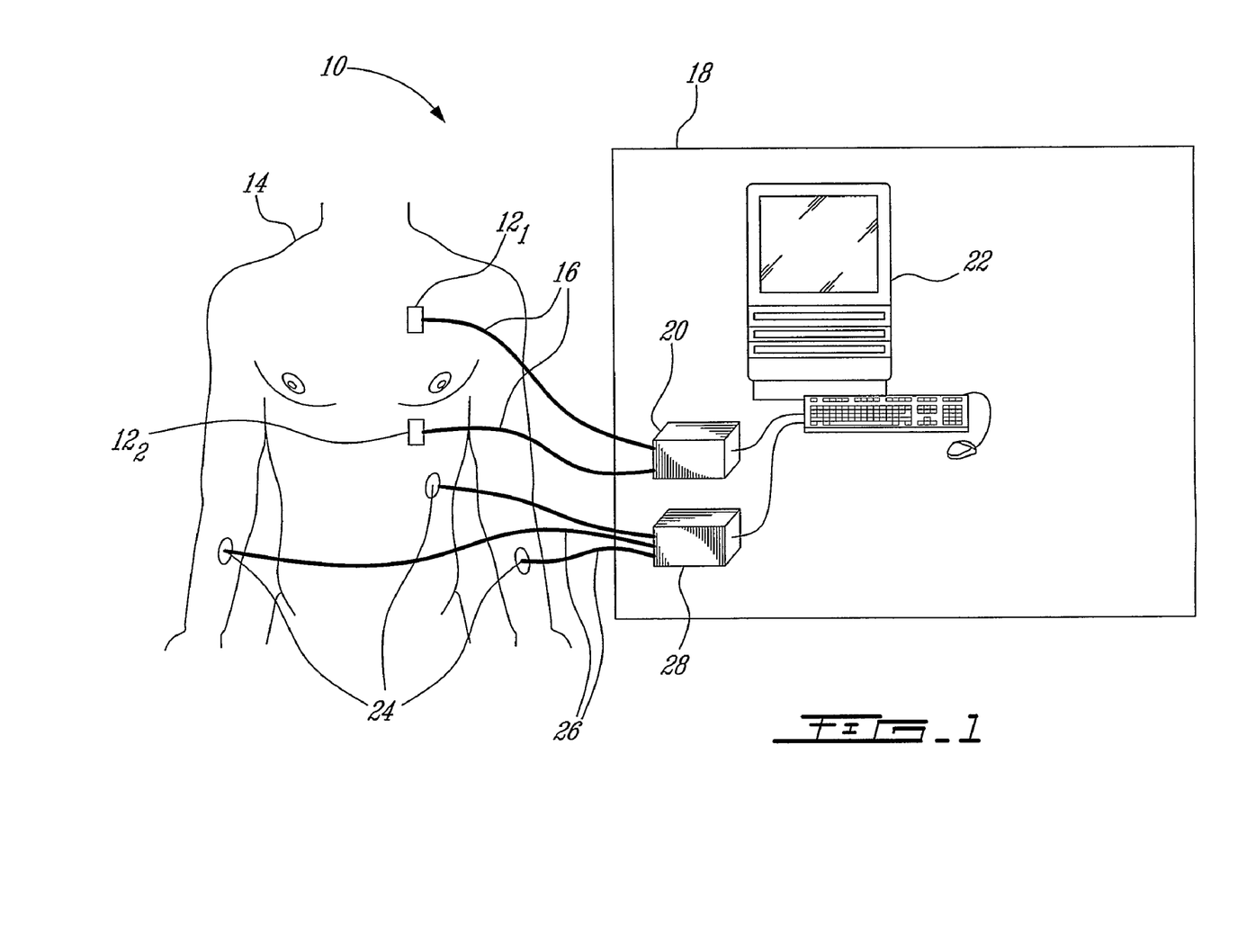
FIG. 1 discloses an illustrative embodiment of a device according to an illustrative embodiment of the present invention.

Referring now to FIG. 1, an illustrative embodiment of a device, generally referred to using the reference numeral 10, will now be described. Illustratively, two identical biological sound sensors 12, for example those described in U.S. Pat. No. 6,661,161 are provided for, although in a given application a single or multiple sensors may be preferable. In the case of the multiple sensor schemas, those sensors are placed at different locations on the patient 14, where we expect to find the maximal intensity of the aortic component of the second heart sound A2 or the pulmonary component of the second heart sound P2 or both A2 and P2 signals. In the illustrated example one sensor $12_1$ is positioned at the apex of heart, where the A2 component of the S2 sound is likely at its maximal in intensity and P2 component is minimal. A second sensor $12_2$ is placed to maximize the P2 component intensity (between the $3^{rd}$ and 4th left intercostal space). The best sensor locations are obtained by experimenting with different positions while observing S2 sound signals, so as to achieve the maximal signal intensity.

The sensors 12 are attached via appropriate leads as in 16 to a data acquisition system 18 comprised of an analog to digital converter 20 and personal computer 22. Data collected by the sensors 12 is digitised by the analog to digital converter 20, illustratively using a sampling rate of 2 kHz with 12 bits of resolution. Additionally, Electrocardiogram (ECG) signals are also collected via a series of electrodes 24, leads 26 and a second analog to digital converter 28. Similar to the acoustic data collected by the biological sound sensors 12, data collected by the ECG electrodes 24 is digitised by the analog to digital converter 28, illustratively using a sampling rate of 2 kHz with 12 bits of resolution. As will be seen below, the electrocardiogram is used as the reference signal to frame the second heart sound (S2).

Figure 2:
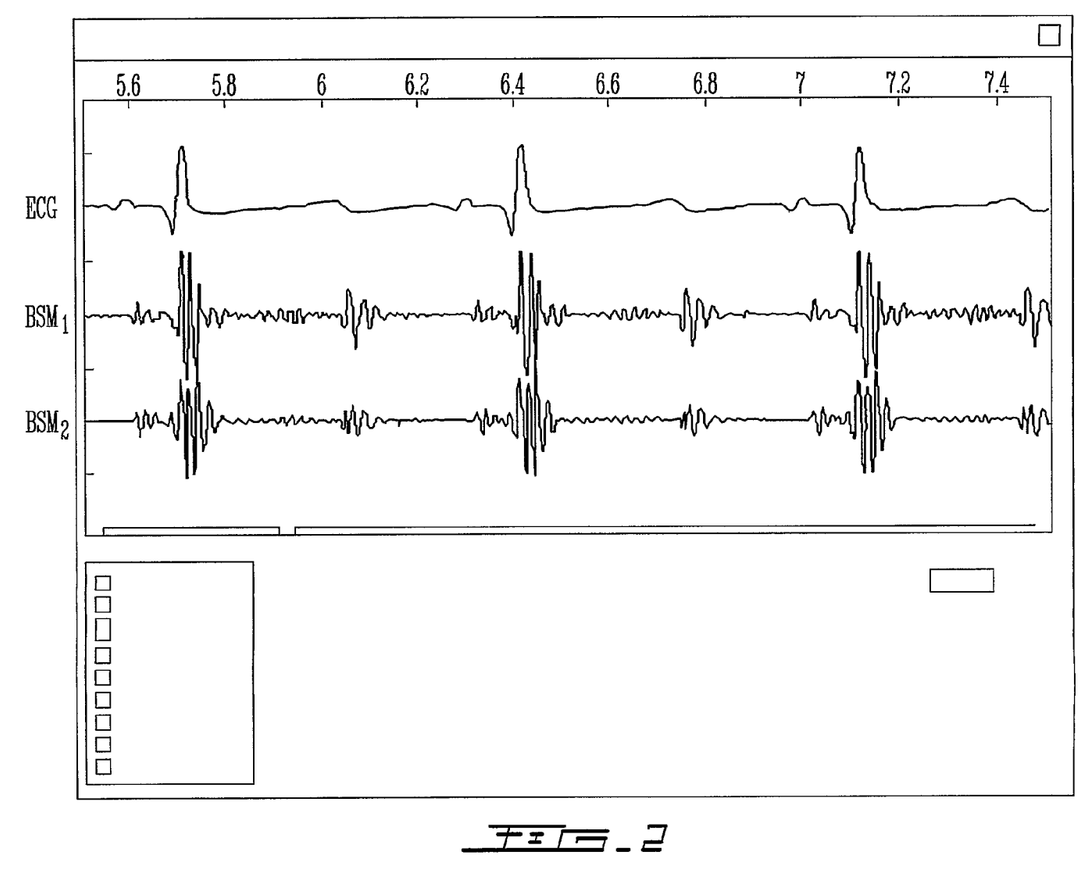
FIG. 2 discloses typical signals detected using an ECG and a pair of biological sound monitors according to an illustrative embodiment of the present invention.

Referring now to FIG. 2, an ECG reading is displayed along side readings from first and second biological sound sensors.

Automatic A2 and P2 Detection

The ECG is used to provide the reference signal to frame the second heart sound. The beat signal in the description below means the part of acoustic signal between two consecutive QRS complexes on the ECG. Depending on the selected approach, the "beat signal" can be defined as the Q-Q' (distance between two Q markers) or as the R-R' (distance between two R markers). In the following description Q-Q' provides the beat signal. For each beat signal the first heart signal (S1) is detected and removed. The remaining sounds, including the second heart sounds and possibly murmurs and the like, are then used as input.

Figure 3A:
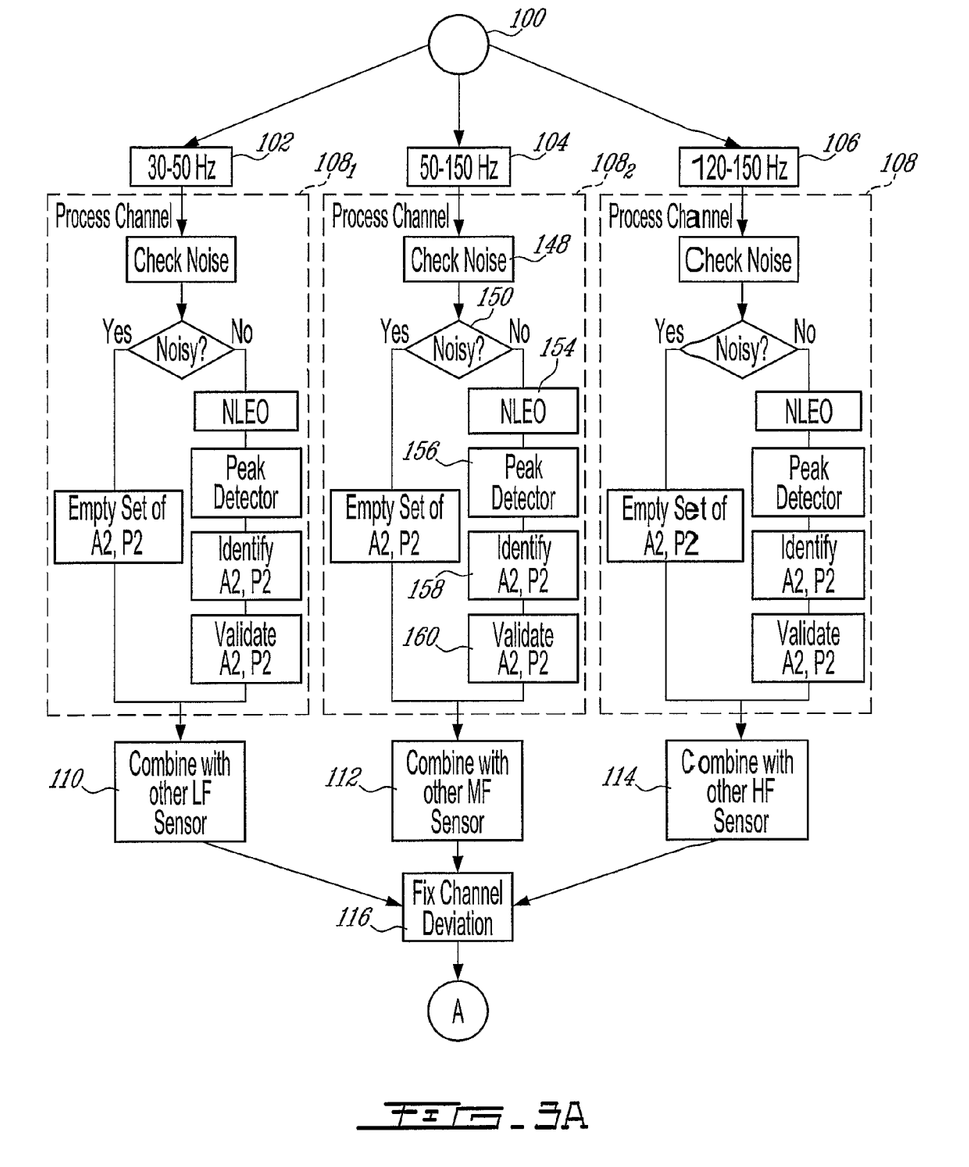
FIGS. 3A and 3B disclose a flow chart of the A2, P2 and SI detection portion of the device according to an illustrative embodiment of the present invention.

Referring now to the flow charts of FIGS. 3A and 3B in addition to FIG. 1, an illustrative embodiment of an approach for detection of the aortic component A2 and the pulmonary component P2 of the second hearts sounds will now be described. The illustrative method supports input signals from the single or multiple sensor(s) 12, each of them comprised of signals of heart sounds in the frequency range 30-200 Hz, although this range could be wider without any changes in the approach. If that range is narrower, however, the method should be adapted to those limitations.

Sounds related to heart beats are collected at 100 via a sensor(s) 12 and illustratively divided into three sub channels 102, 104 and 106 (or frequency bands). These bands are: Low Frequency (LF, 30-50 Hz), Medium Frequency (MF, 50-150 Hz), and High Frequency (HF, 120-200 Hz).

Each sub-channel is relayed to a "Process Channel" block as in $108_1$, $108_2$, and $108_3$, (these will be described separately hereinbelow). The process channel block can be based on a variety of methods including a Chirplet method, Non-linear Energy Operator (NLEO) method, or any other suitable method capable of extracting and discriminating A2 and P2 components from second heart sound S2.

Of note is that the present illustrative embodiment applies the NLEO method.

The output values of A2 and P2 from the process channel blocks as in $108_1$, $108_2$, and $108_3$ are analysed. If both components A2, P2 are clearly detectable in at least one of the sub channels, these are the values for A2, P2. If both components are not clearly detectable then the outputs of the process channel blocks as in $108_1$, $108_2$, and $108_3$ are compared sub-channel by sub-channel with the output of the process channel blocks for other sensors (not shown) of the same sub channels at blocks 110, 112, and 114. In the case at hand, there are illustratively two sensors (the second sensor not shown) the outputs of the process blocks of which are thus compared pair wise.

Illustratively, the comparison is carried out on each frequency band according to the following set of rules, although it should be understood that this is an example and not intended to be limiting:

If the output of 108 for both sensors reveals A2 and P2 components and the positions of A2 and P2 in each sensor output are the same, then these positions provide the values of A2 and P2;

If one of the outputs of 108 for both sensors reveals A2 and P2 components, but the other does not, then the positions of these A2 and P2 provide the values of A2 and P2;

If the output of 108 for both sensors reveals only one A2 or one P2 component then, as it is unknown whether the component is A2 or P2, then the value of A2 is the position of the first component and the value of P2 the position of the second component.

If the output of 108 for one of the sensors reveals both A2 and P2 components while the output of 108 for the other sensor reveals only one (A2 or P2) component, then the readings for both sensors are combined (superimposed).

If the result reveals only two components (A2 and P2) then the positions of these A2 and P2 provide the values of A2 and P2;

If the result still reveals three components (where one or two of the results are A2 and/or P2 and the remainder the result of biological noise), then the readings are combined (superimposed) and the two components with the greatest FWE are selected as A2 and P2, the positions of these A2 and P2 provide the values of A2 and P2.

If the output of 108 for both sensors reveals A2 and P2 components but the positions of A2 and P2 are different, then:

If the Splitting Interval (SI) of both sensors is less than 10 ms then the value of A2 is the position of A2 and the value of P2 is the position of P2 as determined via one of the sensors;

If at least one of the SI from first or second sensor is greater than 10 ms, all components (A2 and P2) within 10 ms are merged.

If only one component results, then the value of both A2 and P2 is the position of this one component and resulting SI is equal to zero;

If two components result, then the value of A2 is the position of the first component and the value of P2 the position of the second component;

If three components result, then the values of A2 and P2 are the positions of the two components with the greatest FWE; and If four components result, then the values of A2 and P2 are the positions of A2 and P2 from the sensor where the amplitude of components FWE is greater than that of the other sensor.

A similar approach is used in the case of multiple sensors.

The SI for each sub-channel, including combined channels, is also calculated.

The A2 and P2 components in the LF, MF, and HF sub-channels have small variations in positioning because of different frequency content. As a result, at block 116, heuristic rules are used to correct those deviations and produce A2 and P2 single values from the combination of A2 and P2 from all sub-channels (LF, MF, HF) as well as any combined values which may have been generated. An illustrative example of the heuristic rules applied at block 116 is as follows:

If no values for both A2 and P2 are available in the MF and HF sub-channels and the SI of the LF channel>120 msec, then discard the SI of the LF channel;

If values for both A2 and P2 are available in the LF and HF sub-channels and the SI of the LF channel>1.4*SI of the HF channel, then discard the SI of the LF channel;

If values for both A2 and P2 are available in the LF and MF sub-channels, and the SI of the LF channel>1.4*the SI of the MF channel, then the SI of the LF channel=1.4*the SI of the MF channel; and If values for both A2 and P2 are available in the MF and HF sub-channels, and the SI of the MF channel<1.4*the SI of the HF channel, then the SI of the HF channel=(1/1.4) *the SI of the MF channel.

Figure 3B:
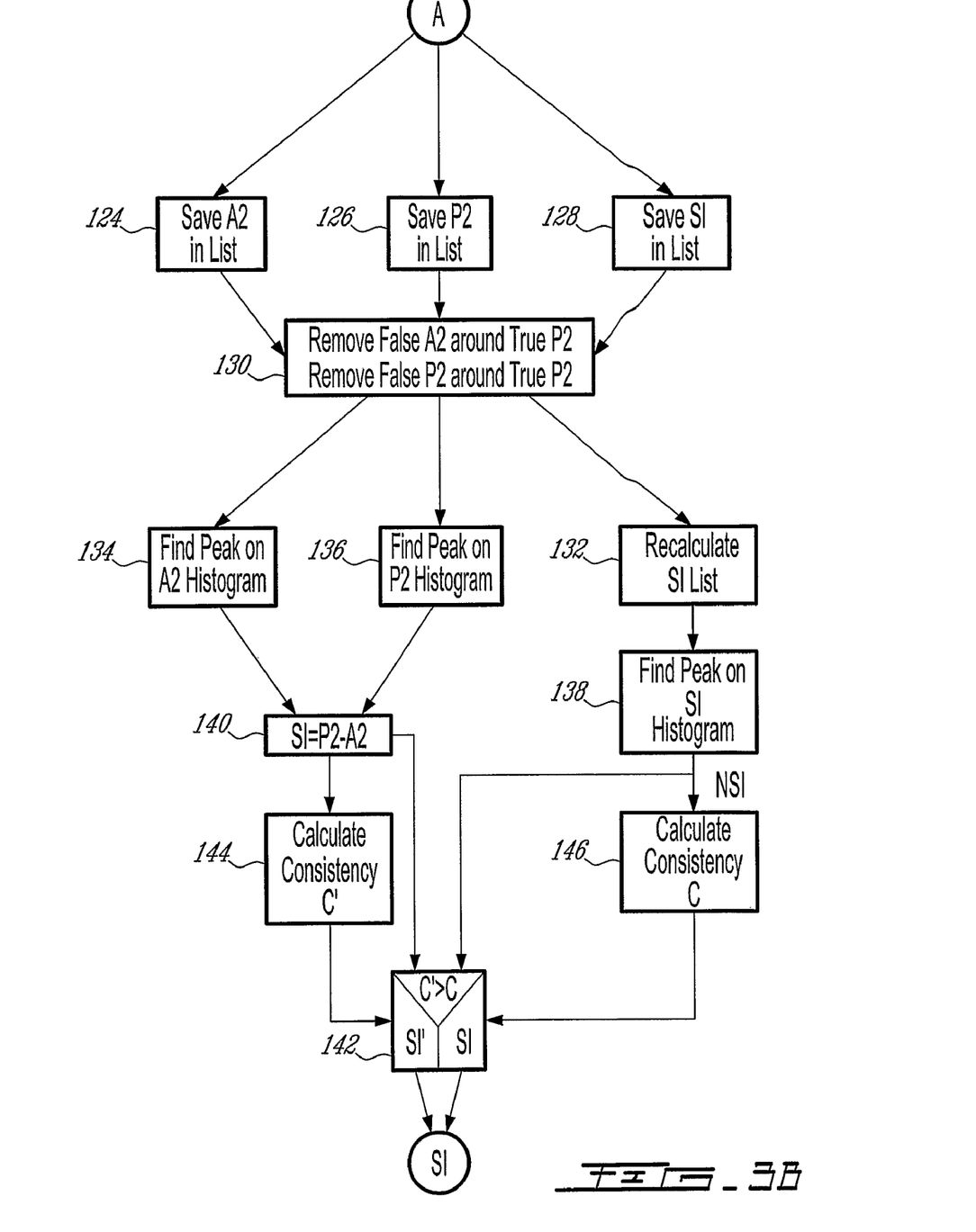

Referring now to FIG. 3B, the values of A2, P2 and SI for the current beat are stored at blocks 124, 126 and 128. Illustratively, values of A2, P2 and SI calculated for beats during the previous minute are retained.

At the same time consistency of solution and signal-to-noise ratio (SNR) for each sub-channel is estimated and stored in separate lists. In this regard, for each sub-range the SNR is estimated. Consistency indicates the percentage of beats not rejected due to high noise. Illustratively, in order to determine the SNR, the S2 sound is first detected as well as the precise position of the start and end of S2. The signal component (S) is calculated as the energy between the start and end of S2, divided by the duration of S2 (in msec). The noise component (N) is calculated as the energy within 50 msec segment before the start of S2 added to the energy within 50 msec segment after the end of S2 divided by 100 msec. The resulting signal-to-noise ratio is calculated as SNR=S/R.

After all beats within the time averaging interval (in the case at hand illustratively 1 minute) have been processed in the above manner, a series of values of A2, P2 and SI are ready for statistical validation. At a first step of the validation process the distributions of A2 and P2 are estimated and a threshold location in time from the start of S2 value T calculated using the bias criterion. Typically between 50-200 beats are present during a one minute sampling interval. Histograms are used in order to provide an estimation of the distributions. The distribution law of SI is used for additional control of the T value in the case of multi-peak distribution of A2 or P2.

At block 130, any values of A2 which are located at a time greater than T from the start of S2 and values of P2 located at a time of less than time T from the Start of S2 are discarded from the stored values. The SI values are then recalculated at block 132 using only those A2 and P2 values which still have pairs.

At blocks 134, 136 and 138 the central peaks on the A2, P2 and SI histograms are estimated using a two-iteration method. During a first iteration the central peak of each histogram is identified. During a second iteration, 20% of the input values, those which are the most distant from each central peak are removed. The histogram is rebuilt using only the remaining input values. Then at block 140 the value SI'=P2−A2 is calculated.

At block 142, SI' is compared with the peak value of SI calculated at block 138. If the difference between SI and SI' is less than 1% of the average beat duration, the mean value of SI and SI' is produced as the final output value for SI. If the difference between SI and SI' is greater than 1% of the average beat duration, the values of SI, SI' having a higher consistency value, as previously calculated at blocks 144, 146 provides the final output value.

Referring back to FIG. 3A, as stated hereinabove, the process channel block 108 can be based on a variety of methods including a Chirplet method, NLEO method, or any other suitable method capable of extracting and discriminating A2 and P2 components from second heart sound S2. Illustratively, the NLEO method is described and comprises the following processing steps. Referring to block $108_2$, The Signal to Noise Ratio (SNR) is determined at block 148. The NLEO method is described in "Adaptive Segmentation of Electroencephalographic Data Using a Nonlinear Energy Operator" by Agarwal, et al., Proceedings IEEE ISCAS '99, Orlando, Fla., 1999, which is incorporated herein by reference.

At decision block 150, if the SNR is below a predetermined value (illustratively 1.5), the current beat in the channel being processed is discarded and no further processing steps carried out. Alternatively, if the SNR is above a predetermined value the NLEO function is calculated at block 154 using the current beat's signal.

In this regard, the NLEO or any other individual implementation of FWE or any other individual implementation of the general family of Autocorrelators may be used.

NLEO is a manipulation of digital signal described in the general case by:

$$\Psi[n]=x(n-l)\cdot x(n-m)-x(n-p)\cdot x(n-q) \text{ for } l+m=p+q \quad (1)$$

One of NLEO's special properties is the ability to compactly describe the notion of a Frequency Weighted Energy (FWE), which is different from the mean-square energy as it reflects both the amplitude as well as the frequency content of a signal. For the special case where l+p=q+m, l≠p and q≠m., given an input of additive white Gaussian noise (AWGN) the expected value of NLEO output is zero. Thus it has the ability to suppress noise. If we consider the case of an amplitude modulated short duration sinusoidal burst in the presence of random noise and structured sinusoidal interference (as in the case of the aortic and the pulmonary components of the S2 sound in the midst of noise), it is anticipated that the NLEO output will enhance FWE of each of these components while suppressing AWGN interference and provide a constant baseline for sinusoidal interference. The time-varying nature of amplitude (Gaussian) and chirping of the dominant rhythm will modulate the NLEO output and produce a detectable burst corresponding to each component in contrast to background clutter. It will then be possible to apply detection strategies on the NLEO output with S2 sound input.

Illustratively, NLEO with parameters l=2, m=1, p=3, q=4 was applied.

Once the NLEO function is calculated, at block 156 the highest peak (maximum of NLEO output for given beat signal) is determined and those peaks having values of less than 0.05 of highest peak value are removed. In this regard, 0.05 provides good results, although other values may also provide adequate results. If more than two peaks remain, the A2 and P2 candidates are identified at block 158. If only one peak is detected, then this is passed to the output and determined as A2 or P2 according to the procedure described hereinabove at paragraph 18.

Finally, at block 160 the values of A2 and P2 are validated using list of heuristic rules. An illustrative example of such rules are:
  If the time interval between A2 and P2 on NLEO is greater than 100 msec, the component with lower FWE is considered invalid; and
  if the time interval between A2 and P2 on NLEO is less than 10 msec, the component having a lower FWE is considered invalid.

Although the present invention has been described hereinabove by way of an illustrative embodiment thereof, this embodiment can be modified at will, within the scope of the present invention, without departing from the spirit and nature of the subject of the present invention.

What is claimed is:

1. A method for estimating a location of pulmonary and aortic components of second heart sounds of a patient over an interval, the method comprising the steps of:
  producing an electronic representation of heart sounds of the patient over the interval;
  identifying at least one second heart sound in the interval using said electronic representation;
  for each identified second heart sound:
    calculating a frequency weighted energy (FWE);
    normalizing said FWE;
    identifying peaks in said FWE;
    determining a maximum peak from said identified peaks; and
    retaining said maximum peak and peaks having an amplitude within a predetermined amount of an amplitude of said maximum peak;
    wherein if two or more peaks are retained, two largest peaks are selected, a first peak as a candidate value for the aortic component and a second peak as a candidate value for the pulmonary component, wherein said first peak is prior to said second peak and wherein if only a single peak is retained, said single peak is selected as a candidate value for the aortic component; and
  generating an estimated value for a location of the aortic component and the pulmonary component from said candidate values;
  wherein said FWE calculating step comprises generating a Non Linear Energy Operator (NLEO) function for each identified second heart sound; and
  wherein in said peak identifying step, a maximum peak value is identified and any identified peaks having a value less than a predetermined amount of said maximum peak value are discarded.

2. A method for estimating a location of pulmonary and aortic components of second heart sounds of a patient over an interval, the method comprising the steps of:
  producing an electronic representation of heart sounds of the patient over the interval;
  identifying at least one second heart sound in the interval using said electronic representation;
  for each identified second heart sound:
    calculating a frequency weighted energy (EWE);
    normalizing said FWE;
    identifying peaks in said FWE;

determining a maximum peak from said identified peaks; and retaining said maximum peak and peaks having an amplitude within a predetermined amount of an amplitude of said maximum peak;

wherein if two or more peaks are retained, two largest peaks are selected, a first peak as a candidate value for the aortic component and a second peak as a candidate value for the pulmonary component, wherein said first peak is prior to said second peak and wherein if only a single peak is retained, said single Leak is selected as a candidate value for the aortic component;

generating an estimated value for a location of the aortic component and the pulmonary component from said candidate values;

for each identified second heart sound and prior to said FWE calculating step, a signal to noise ratio (SNR) calculating step wherein when said calculated SNR is below a predetermined ratio, no candidate values for the aortic component or the pulmonary component are selected;

wherein said SNR calculating step comprises detecting a start and finish of said identified second heart sound, calculating an average signal energy between said start and finish, calculating an average noise energy for a predetermined period before said start and after said finish, wherein said SNR is equal to said average signal energy divided by said average noise energy; and wherein said predetermined period is 50 ms.

3. A method for estimating a location of pulmonary and aortic components of second heart sounds of a patient over an interval, the method comprising the steps of:

producing an electronic representation of heart sounds of the patient over the interval;

identifying at least one second heart sound in the interval using said electronic representation;

for each identified second heart sound:
calculating a frequency weighted energy (FWE);
normalizing said FWE;
identifying peaks in said FWE;
determining a maximum peak from said identified peaks; and
retaining said maximum peak and peaks having an amplitude within a predetermined amount of an amplitude of said maximum peak;
wherein if two or more peaks are retained, two largest peaks are selected, a first peak as a candidate value for the aortic component and a second peak as a candidate value for the pulmonary component, wherein said first peak is prior to said second peak and wherein if only a single peak is retained, said single peak is selected as a candidate value for the aortic component;

generating an estimated value for a location of the aortic component and the pulmonary component from said candidate values;

for each identified second heart sound and prior to said FWE calculating step, a signal to noise ratio (SNR) calculating step wherein when said calculated SNR is below a predetermined ratio, no candidate values for the aortic component or the pulmonary component are selected; and wherein said predetermined ratio is 0.50.

4. A method for estimating pulmonary artery pressure of a patient over an interval, the method comprising the steps of:
producing an electronic representation of heart sounds of the patient over the interval;
identifying at least one second heart sound in the interval using said electronic representation;
for each identified second heart sound:
calculating a FWE;
normalizing said FWE;
identifying peaks in said FWE;
determining a maximum peak from said identified peaks; and
retaining said maximum peak and peaks having an amplitude within a predetermined amount of an amplitude of said maximum peak;
wherein if two or more peaks are retained, two largest peaks are selected, a first peak as a candidate value for the aortic component and a second peak as a candidate value for the pulmonary component, wherein said first peak is prior to said second peak and wherein if only a single peak is retained, said single peak is selected as a candidate value for the aortic component; and generating an estimated value for a location of an aortic component and a location of pulmonary component from said candidate values;

determining a splitting interval as a time between said aortic component location and said pulmonary component location;

normalizing said splitting interval; and estimating the systolic pulmonary artery pressure using a predetermined function which describes a relationship between said normalized splitting interval and the systolic and diastolic pulmonary artery pressures.

5. A device for estimating a location of pulmonary and aortic components of second heart sounds of a patient over an interval, the device comprising:

at least one transducer for sensing heart sounds of the patient, said heart sounds comprising, during motion of the patient, a first sound portion indicative of second heart sounds and a second sound portion indicative of motion induced noise; and a second heart sound processor to identify second heart sounds from said sensed heart sounds and compute an aortic component location and an estimated pulmonary component location from said identified second heart sounds without significant interference in said identification and computation from the motioned induced noise portion of said sensed heart sounds;

wherein said second heart sound processor comprises:
a means for identifying at least one second heart sound in the interval using said sensed heart sounds;
a means for calculating a frequency weighted energy (FWE) of each identified second heart sound;
a means for normalizing said calculated FWE of each identified second heart sound;
a means for identifying peaks in said calculated FWE of each identified second heart sound and determining a maximum peak from said identified peaks; and
a means for retaining said maximum peak and peaks having an amplitude within a predetermined amount of an amplitude of said maximum peak wherein if two or more peaks are retained, two largest peaks are selected, a first peak as a candidate value for the aortic component and a second peak as a candidate value for the pulmonary component, wherein said first peak is prior to said second peak and wherein if only a single peak is retained, said single peak is selected as a candidate value for the aortic component; and a means for generating an estimated value for a location of the aortic component and the pulmonary component from said candidate values;

wherein said FWE calculating means generates a Non Linear Energy Operator (NLEO) function for each identified second heart sound; and wherein said peak identifying means identifies a maximum peak value and discards any identified peak having a value less than a predetermined amount of said maximum peak value.

* * * * *